US012564577B2

(12) United States Patent
Venkatraman et al.

(10) Patent No.: US 12,564,577 B2
(45) Date of Patent: Mar. 3, 2026

(54) NANOLIPOSOMES FOR SUSTAINED DELIVERY OF TACROLIMUS FOR TREATMENT OF ANTERIOR SEGMENT EYE DISEASES

(71) Applicants: Nanyang Technological University, Singapore (SG); Singapore Health Services Pte Ltd, Singapore (SG)

(72) Inventors: Subramanian Venkatraman, Singapore (SG); Jayaganesh V. Natarajan, Singapore (SG); Yin Chiang Freddy Boey, Singapore (SG); Jodhbir Singh Mehta, Singapore (SG); Tina Tzee Ling Howden, Singapore (SG); Xu Wen Ng, Singapore (SG); Anthony Herr Cheun Ng, Singapore (SG)

(73) Assignees: Nanyang Technological University, Singapore (SG); Singapore Health Services Pte Ltd, Singapore (SG)

( * ) Notice: Subject to any disclaimer, the term of this patent is extended or adjusted under 35 U.S.C. 154(b) by 316 days.

(21) Appl. No.: 18/308,557

(22) Filed: Apr. 27, 2023

(65) Prior Publication Data

US 2023/0263780 A1 Aug. 24, 2023

Related U.S. Application Data

(62) Division of application No. 16/094,827, filed as application No. PCT/SG2017/050216 on Apr. 19, 2017, now Pat. No. 11,672,784.

(51) Int. Cl.

| | |
|---|---|
| ***A61K 31/436*** | (2006.01) |
| ***A61K 9/00*** | (2006.01) |
| ***A61K 9/127*** | (2025.01) |
| ***A61K 9/51*** | (2006.01) |
| ***A61P 27/04*** | (2006.01) |

(52) U.S. Cl.

CPC .......... *A61K 31/436* (2013.01); *A61K 9/0048* (2013.01); *A61K 9/127* (2013.01); *A61K 9/5123* (2013.01); *A61P 27/04* (2018.01)

(58) Field of Classification Search

CPC .... A61K 31/436; A61K 9/0048; A61K 9/127; A61K 9/5123; A61K 9/0051; A61P 27/04

See application file for complete search history.

(56) References Cited

U.S. PATENT DOCUMENTS

| | | | | |
|---|---|---|---|---|
| 5,817,333 | A | 10/1998 | Kagayama et al. | |
| 6,579,901 | B2 | 6/2003 | Chen et al. | |
| 6,984,397 | B2 | 1/2006 | Fujisaki et al. | |
| 2002/0013340 | A1 | 1/2002 | Peyman | |
| 2003/0018044 | A1 | 1/2003 | Peyman | |
| 2004/0224010 | A1 | 11/2004 | Hoffand et al. | |
| 2006/0110441 | A1 | 5/2006 | Wong et al. | |
| 2009/0136514 | A1* | 5/2009 | Power | A61K 31/65 424/145.1 |
| 2009/0317455 | A1 | 12/2009 | Oku et al. | |
| 2011/0212167 | A1 | 9/2011 | Ali et al. | |
| 2013/0216606 | A1* | 8/2013 | Venkatraman | A61K 9/127 514/530 |

FOREIGN PATENT DOCUMENTS

| | | | |
|---|---|---|---|
| CN | 103142468 | A | 6/2013 |
| EP | 1 159 962 | A1 | 12/2001 |
| EP | 2 058 009 | A1 | 5/2009 |

OTHER PUBLICATIONS

Linares-Alba et al., "Preformulation Studies of a Liposomal Formulation Containing Sirolimus for the Treatment of Dry Eye Disease," *Journal of Ocular Pharmacology and Therapeutics* 32(1):11-22, 2016. (13 pages).

Mishra et al. "Recent Applications of Liposomes in Ophthalmic Drug Delivery," *Journal of Drug Delivery 2011* (863734), 14 pages.

* cited by examiner

*Primary Examiner* — Frederick F Krass
*Assistant Examiner* — Abdulrahman Abbas
(74) *Attorney, Agent, or Firm* — Morgan, Lewis & Bockius LLP

(57) ABSTRACT

According to the present disclosure, the use of a nanoliposome in the manufacture of a medicament for the prophylaxis and/or treatment of anterior segment ocular diseases is provided. The nanoliposome comprises a plurality of unsaturated and/or saturated lipids forming at least one lipid bilayer encapsulating a hydrophobic drug comprising tacrolimus, wherein the hydrophobic drug and the plurality of unsaturated and/or saturated lipids have a weight ratio of up to 0.2. The present disclosure also provides for such a nanoliposome and a method of preventing and/or treating anterior segment ocular diseases based on the nanoliposomes.

11 Claims, 3 Drawing Sheets

NANOLIPOSOMES FOR SUSTAINED DELIVERY OF TACROLIMUS FOR TREATMENT OF ANTERIOR SEGMENT EYE DISEASES

CROSS-REFERENCE TO RELATED APPLICATION

This application claims the benefit of priority of Singapore Patent Application No. 10201603094P, filed 19 Apr. 2016, the content of it being hereby incorporated by reference in its entirety for all purposes.

TECHNICAL FIELD

The present disclosure generally relates to a nanoliposome comprising a hydrophobic drug such as tacrolimus and the nanoliposome's use in the prevention and/or treatment of anterior segment ocular diseases.

BACKGROUND

Tacrolimus (also known as FK506 or FK-506) is a macrolactum derivative with immunomodulatory and anti-inflammatory activity. Tacrolimus has been used in eye drops and topical tacrolimus eye drops have been routinely used in clinics for management of various anterior segment eye diseases. Generally, the tacrolimus eye drops may be used to treat seasonal allergies (e.g. conjunctivitis), ocular surface diseases (e.g. dry eye), post-operative management of trabeculectomy and in graft rejection. Although prolonged use of the eye drops tend to be necessary for better therapeutic response, it may lead to complications such as side effects and patient incompliance. For example, some potential drawbacks of using eye drops too often may be sub-optimal management of the aforementioned conditions or diseases, and/or serious side effects such as permanent redness or damage to blood vessels in the eye.

To mitigate the prolonged use or abuse of the eye drops, an alternative treatment strategy of providing sustained release of tacrolimus needs to be developed. The treatment strategy also needs to minimize invasive and/or risky administration (e.g. intravitreal injection) of tacrolimus.

Based on the above, there is thus a need to provide for a drug delivery means which possesses the above advantages while ameliorating one or more of the drawbacks as mentioned above.

SUMMARY

In one aspect, there is disclosed the use of a nanoliposome in the manufacture of a medicament for the prophylaxis and/or treatment of anterior segment ocular diseases, wherein the nanoliposome comprises a plurality of unsaturated and/or saturated lipids forming at least one lipid bilayer encapsulating a hydrophobic drug comprising tacrolimus, and wherein the hydrophobic drug and the plurality of unsaturated and/or saturated lipids have a weight ratio of up to 0.2.

In another aspect, there is disclosed a nanoliposome for use in the prophylaxis and/or treatment of anterior segment ocular diseases, wherein the nanoliposome comprises a plurality of unsaturated and/or saturated lipids forming at least one lipid bilayer encapsulating a hydrophobic drug comprising tacrolimus, and wherein the hydrophobic drug and the plurality of saturated and/or unsaturated lipids have a weight ratio of up to 0.2.

In another aspect, there is disclosed a method of preventing and/or treating anterior segment ocular diseases by administering a nanoliposome comprising a plurality of unsaturated and/or saturated lipids forming at least one lipid bilayer encapsulating a hydrophobic drug comprising tacrolimus, wherein the hydrophobic drug and the plurality of saturated and/or unsaturated lipids have a weight ratio of up to 0.2.

BRIEF DESCRIPTION OF THE DRAWINGS

In the drawings, like reference characters generally refer to like parts throughout the different views. The drawings are not necessarily to scale, emphasis instead generally being placed upon illustrating the principles of the invention. In the following description, various embodiments of the present disclosure are described with reference to the following drawings, in which:

FIG. 5 shows tacrolimus is encapsulated in the lipid bilayer.

DETAILED DESCRIPTION

Figure 1:
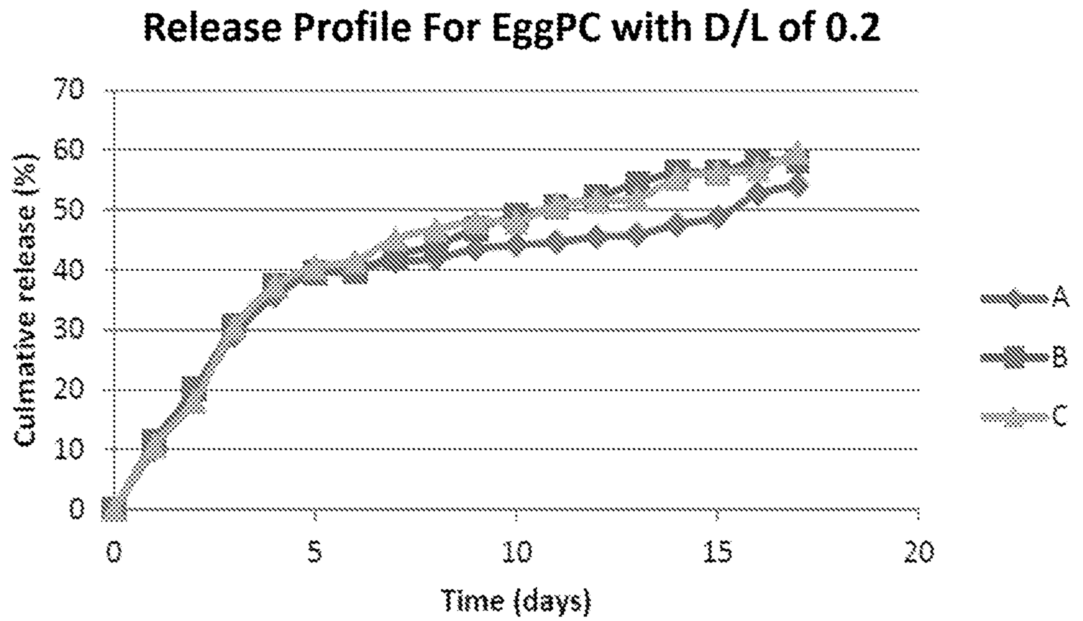
FIG. 1 shows a cumulative percentage tacrolimus release (%) plot against time (days). This plot features an in vitro drug release profile of tacrolimus loaded egg yolk phosphatidylcholine (EggPC) liposomes for three independent samples (labelled as A, B and C) made according to the embodiments disclosed herein. For each sample, 1 ml of liposomes was dialysed against 40 ml PBS with a pH of 7.4.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and changes may be made without departing from the scope of the invention. The various embodiments are not necessarily mutually exclusive, as some embodiments can be combined with one or more other embodiments to form new embodiments.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

In the present disclosure, sustained release nanoliposomes encapsulating tacrolimus have been developed as an effective treatment strategy for various anterior segment ocular diseases. Non-limiting examples of such diseases may include, inflammatory conditions in the anterior eye segment (e.g. allergic conjunctivitis), ocular surface problems (e.g. dry eye), and conditions associated with lack of immunosuppression (e.g. post corneal graft). The nanoliposomes of the present disclosure may be applied via a less risky procedure such as subconjunctival injection instead of intravitreal injection.

Advantageously, by using the sustained release nanoliposomes as disclosed herein, issues associated with existing clinical treatment strategies that require the use of tacrolimus eye drops on a daily basis for prolonged therapeutic efficacy can be circumvented. Not only is the need to apply eye drops avoided because the nanoliposomes can be applied via subconjunctival injection, the drugs are also likely to be released over a longer period of time (e.g. days to months) and thus the therapeutic response can be managed more effectively. This drastically improves patient compliance and minimizes potential side effects arising from frequent eye drops applications required to halt diseases' progression.

With the above in mind, the present disclosure provides for the use of a nanoliposome in the manufacture of a medicament for the prophylaxis and/or treatment of anterior segment ocular diseases. The present disclosure also provides for such a nanoliposome for use in the prophylaxis and/or treatment of anterior segment ocular diseases. The present disclosure further provides for a method of preventing and/or treating anterior segment ocular diseases by administering such a nanoliposome. Embodiments described in the context of the nanoliposome and its uses are analogously valid for the method of treating as described herein, and vice versa.

Before going into the details of the nanoliposome and its uses, the method of treating based on such nanoliposome and the various embodiments, the definitions of certain terms, expressions or phrases are first discussed.

In the context of the present disclosure, the term "nanoliposome" refers to a liposome that has a size of at most 200 nm.

In the context of the present disclosure, the term "hydrophobic" refers to materials or substances that are not soluble and/or swellable with water. Hence, "hydrophobic" materials or substances tend to be immiscible with water and/or tend to maintain a separate distinct phase from water. In this regard, the phrase "immiscible" means that the materials or substances do not mix and/or tend to separate when left to stand.

The expression of "up to" when used with reference to numerical values may be understood as less than or equal to that numerical value. In other words, this expression is inclusive of the numerical value it refers to. For example, "up to 0.2" would cover instances that may be less than 0.2 and instances which are equal 0.2.

The word "substantially" does not exclude "completely" e.g. a composition which is "substantially free" from Y may be completely free from Y. Where necessary, the word "substantially" may be omitted from the definition of the invention.

In the context of various embodiments, the articles "a", "an" and "the" as used with regard to a feature or element include a reference to one or more of the features or elements.

In the context of various embodiments, the term "about" or "approximately" as applied to a numeric value encompasses the exact value and a reasonable variance.

As used herein, the term "and/or" includes any and all combinations of one or more of the associated listed items.

As used herein, the phrase of the form of "at least one of A and B" may include A or B or both A and B. Correspondingly, the phrase of the form of "at least one of A and B and C", or including further listed items, may include any and all combinations of one or more of the associated listed items.

Unless specified otherwise, the terms "comprising" and "comprise", and grammatical variants thereof, are intended to represent "open" or "inclusive" language such that they include recited elements but also permit inclusion of additional, unrecited elements. Meanwhile, the terms "consisting" and "consist", and grammatical variants thereof, are intended to represent "close" or "exclusive" language such that they solely include the recited elements but exclude additional, unrecited elements.

Having defined the various terms, expressions and phrases, details of the present nanoliposome and its uses, the method of treating based on such nanoliposome and the various embodiments are now described below.

In the present disclosure, there is disclosed the use of a nanoliposome in the manufacture of a medicament for the prophylaxis and/or treatment of anterior segment ocular diseases, wherein the nanoliposome comprises a plurality of unsaturated and/or saturated lipids forming at least one lipid bilayer encapsulating a hydrophobic drug comprising tacrolimus, and wherein the hydrophobic drug and the plurality of unsaturated and/or saturated lipids have a weight ratio of up to 0.2.

The hydrophobic drug may be loaded in the nanoliposome up to a concentration of 1 mg/ml, 0.5 mg/ml, 0.1 mg/ml, or any other loadings within these ranges. Hence, the nanoliposome may have a drug loading of up to 1 mg/ml according to various embodiments. The hydrophobic drug loaded may be a concoction of one or more hydrophobic drugs. In some instances, the hydrophobic drug loaded may comprise or consist of tacrolimus. The structure of tacrolimus is shown below.

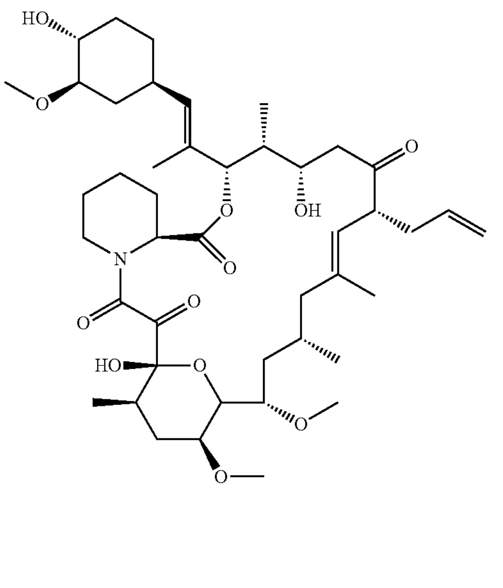 [SMILES: C=CC[C@@H]1/C=C(\C)C[C@H](C)C[C@H](OC)C2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

The hydrophobic drug may be encapsulated in the nanoliposome. The nanoliposome may be formed with at least one lipid bilayer. The lipid bilayer may comprise or consist of a plurality of unsaturated and/or saturated lipids. Accordingly, the hydrophobic drug(s) may be encapsulated in the lipid bilayer. For instance, tacrolimus may be encapsulated between the hydrophobic tails of the lipids that form the bilayer or any other location within the bilayer.

In various embodiments, the plurality of unsaturated and/or saturated lipids may be selected from the group consisting of phosphocholines and sphingolipids. In some instances, the unsaturated lipids may comprise or consist of phosphocholines and/or sphingolipids. In other instances, the saturated lipids may comprise or consist of phosphocholines and/or sphingolipids.

The phosphocholines may be selected from the group consisting of egg yolk phosphatidylcholine (EggPC), 1-palmitoyl-2-oleoyl-sn-glycero-3-phosphocholine (POPC), 1,2-dioleoyl-sn-glycero-3-phosphocholine (DOPC) and dipalmitoylphosphatidylcholine (DPPC). Other suitable phosphocholines may also be used to form the at least one bilayer of the nanoliposome. Meanwhile, sphingolipids may include sphingomyelins, sphingosines, ceramides etc.

In preferred embodiments, the plurality of unsaturated and/or saturated lipids may comprise or consist of at least one unsaturated lipid constituting more than 50 wt % of the at least one lipid bilayer.

Nanoliposomes which demonstrate better sustained release of hydrophobic drug(s) (e.g. tacrolimus) over prolonged periods (e.g. several days), may preferably have an unsaturated lipid tail attached to a PC "head" as the major constituent. The PC "head" may be understood as a phosphatidylcholine (PC) which incorporates choline as a head group. According to preferred embodiments, the at least one unsaturated lipid constituting more than 50 wt % of the at least one lipid bilayer may be composed of a phosphatidylcholine (PC) that incorporates choline as a head group. The structure of a non-limiting exemplary unsaturated lipid having a choline group (e.g. POPC) is shown below.

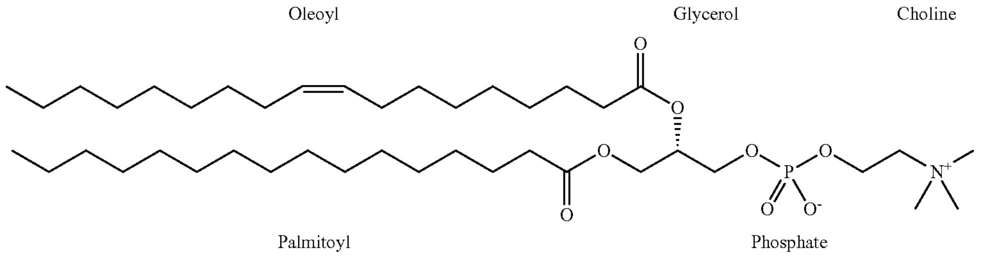 [SMILES: CCCCCCCC/C=C\CCCCCCCC(=O)O[C@@H](COC(=O)CCCCCCCCCCCCCCC)COP(=O)([O-])OCC[N+](C)(C)C]

EggPC, as used in various embodiments disclosed herein, may typically contain about more than 50 wt % or even about 95 wt % of POPC and/or other PCs with unsaturated tails, along with about 50 wt % or less, or even about 5 wt % of sphingomyelin which has an unsaturated tail. The structures of some major constituents possibly present in EggPC are shown below.

1-palmitoyl-2-oleoyl-sn-glycero-3-phosphocholine (POPC):

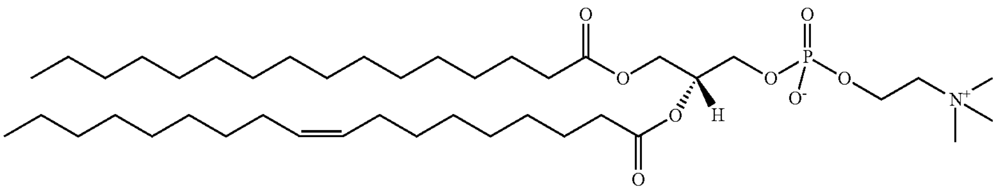

Phosphatidylethanolamine (PE):

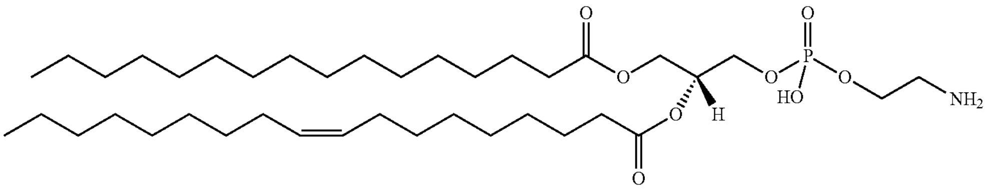

-continued

Sphingomyelin:

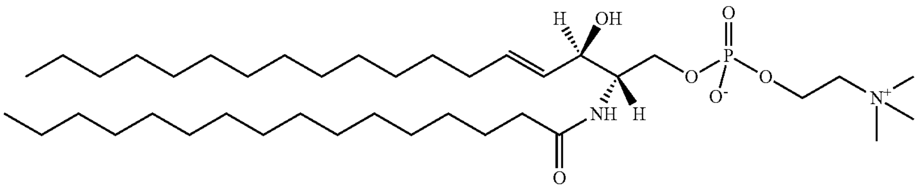

1,2-dioleoyl-sn-glycero-3-phosphocholine (DOPC or di-oleyl):

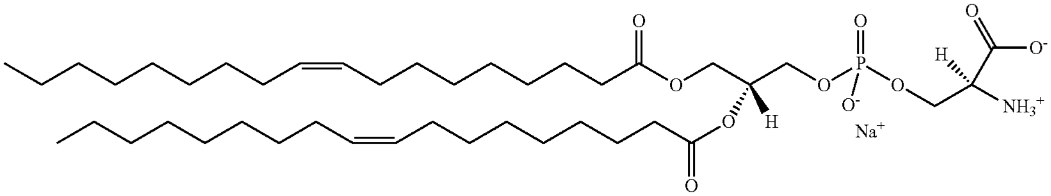

Dipalmitoylphosphatidylcholine (DPPC):

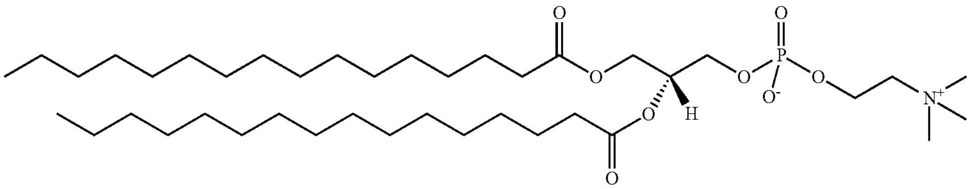

Notwithstanding the various lipids illustrated, the drug release profile of nanoliposomes consisting of fully saturated lipids may not be ideal. Thus, lipids used to form nanoliposomes may preferably contain unsaturated lipid(s) or a mixture of lipids having at least one unsaturated lipid as the major component. Preferred unsaturated lipids may include, but not limited to, POPC, DOPC, sphingolipids etc. Meanwhile, saturated lipids may form the minor components of the nanoliposome. That is to say, saturated lipids in the nanoliposome may be present at about 50 wt % or less than 50 wt %.

Depending on the type of unsaturated and/or saturated lipids utilized, the nanoliposome may have different sizes. The size of the nanoliposome may change insignificantly after storage.

In various embodiments, the nanoliposome may have an average size of 80 nm to 150 nm, 85 nm to 110 nm, 85 nm to 105 nm, 85 nm to 100 nm, 90 nm to 115 nm, 90 nm to 100 nm, 90 nm to 95 nm, or any other average sizes falling within these specified ranges. Other sizes may be possible depending on the lipids used. The nanoliposome may have a size falling within these ranges before storage, with or without drug loaded. In various instances, the nanoliposomes may have any of these average sizes before storage at 4° C. For example, EggPC nanoliposomes may be 89.64 nm±0.78 nm before storage (e.g. storing at 4° C.). In another example, DPPC nanoliposomes may be 106.37 nm±1.00 nm before storage (e.g. storing at 4° C.).

In various other embodiments, the nanoliposome(s) may have an average size of 90 nm to 120 nm, 90 nm to 110 nm, 90 nm to 100 nm, 100 nm to 120 nm, 110 nm to 120, or any other average sizes falling within these specified ranges after storage. Other sizes may be possible depending on the lipids used. The nanoliposome may have a size falling within these ranges after storage, with or without drug loaded. In various instances, the nanoliposomes may have any of these average sizes after storing (e.g. at 4° C.) for a certain duration (days or months). For example, EggPC nanoliposomes may be 90.67 nm±0.49 nm after storage (e.g. at 4° C.). In another example, DPPC nanoliposomes may be 112.8 nm±1.05 nm after storage (e.g. at 4° C.).

Based on the change of sizes before and after storage (e.g. at 4° C.), the nanoliposomes may be advantageously stored for extended periods of time, even with the drug loaded, without having its structural and the drug integrity compromised. In various instances, the size of a nanoliposome may refer to its diameter.

Apart from the size, the type of lipids used may influence the polydispersity index of the nanoliposome. The polydispersity of the nanoliposome may change insignificantly after storage.

In various embodiments, the nanoliposome may have a polydispersity index of less than 0.3, 0.2 or even 0.1 before and after storage. Other polydispersity index may be possible based on the type of lipids used. In some instances, EggPC nanoliposomes may have a polydispersity index of 0.052±0.018 before storage while DPPC nanoliposomes may have a polydispersity index of 0.28±0.016 before storage. After storage (e.g. at 4° C.), the EggPC nanoliposomes may have a polydispersity index of 0.014±0.007 while the DPPC nanoliposomes may have a polydispersity index of 0.218±0.036 according to various instances. Based on the polydispersity index before and after storage (e.g. at 4° C.), this again demonstrates the present nanoliposomes may be stored for extended periods of time, even with the drug loaded, without having the integrity of the nanoliposome and the drug compromised.

According to various embodiments, the nanoliposome as described above may be a multilamellar vesicle or an unilamellar vesicle.

As mentioned above, the present disclosure also relates to a nanoliposome for use in the prophylaxis and/or treatment of anterior segment ocular diseases, wherein the nanoliposome comprises a plurality of unsaturated and/or saturated lipids forming at least one lipid bilayer each encapsulating a hydrophobic drug comprising tacrolimus, and wherein the hydrophobic drug and the plurality of saturated and/or unsaturated lipids have a weight ratio of up to 0.2. Embodiments relating to the nanoliposome have been described above and are reiterated below.

The nanoliposome may have a drug loading of up to 1 mg/ml, 0.5 mg/ml, 0.1 mg/ml, or any other loadings within these ranges. The hydrophobic drug may be a concoction of one or more hydrophobic drugs. The hydrophobic drug may comprise or consist of tacrolimus.

The hydrophobic drug may be encapsulated in the nanoliposome, wherein the nanoliposome may have at least one lipid bilayer formed from the plurality of unsaturated and/or saturated lipids. Accordingly, the hydrophobic drug(s) may be encapsulated in the lipid bilayer. For instance, tacrolimus may be encapsulated between the hydrophobic tails of the lipids that form the bilayer or any other location within the bilayer.

The plurality of unsaturated and/or saturated lipids may be selected from the group consisting of phosphocholines and sphingolipids. The phosphocholines may be selected from the group consisting of egg yolk phosphatidylcholine (EggPC), 1-palmitoyl-2-oleoyl-sn-glycero-3-phosphocholine (POPC), 1,2-dioleoyl-sn-glycero-3-phosphocholine (DOPC) and dipalmitoylphosphatidylcholine (DPPC). The constituents of EggPC have been described above. Other suitable phosphocholines may be used to form the at least one bilayer of the nanoliposome. Meanwhile, sphingolipids may include sphingomyelins, sphingosines, ceramides etc.

In preferred embodiments, the plurality of unsaturated and/or saturated lipids may comprise or consist of at least one unsaturated lipid constituting more than 50 wt % of the at least one lipid bilayer.

Preferred embodiments of nanoliposomes which demonstrate better sustained release of hydrophobic drug(s) (e.g. tacrolimus) over prolonged periods (e.g. several days) may comprise or consist of an unsaturated lipid tail attached to a PC "head" as the major constituent. This means that the at least one unsaturated lipid constituting more than 50 wt % of the at least one lipid bilayer may be composed of a phosphatidylcholine (PC) that incorporates choline as a head group.

Depending on the type of unsaturated or saturated lipids utilized, the nanoliposome may have different sizes before or after storage. The size of the nanoliposome may change insignificantly after storage.

The nanoliposome may have an average size of 80 nm to 150 nm, 85 nm to 110 nm before storage (e.g. at 4° C.). Embodiments concerning other sizes or range of sizes before storage have been described above.

The nanoliposome may have an average size of 90 nm to 120 nm after storage (e.g. at 4° C.). Embodiments concerning other sizes or range of sizes after storage (e.g. at 4° C.) have been described above.

As explained above, the type of lipids used may influence the polydispersity index of the nanoliposome. The polydispersity of the nanoliposome may change insignificantly after storage. In various embodiments, the nanoliposome may have a polydispersity index of less than 0.3, 0.2 or even 0.1 before and after storage. Non-limiting embodiments based on EggPC nanoliposomes and DPPC nanoliposomes before and after storage have been described above.

The nanoliposome may be a multilamellar vesicle or an unilamellar vesicle according to various embodiments disclosed herein.

As mentioned above, the present disclosure further relates to a method of preventing and/or treating anterior segment ocular diseases by administering a nanoliposome comprising a plurality of unsaturated and/or saturated lipids forming at least one lipid bilayer encapsulating a hydrophobic drug comprising tacrolimus, wherein the hydrophobic drug and the plurality of saturated and/or unsaturated lipids have a weight ratio of up to 0.2.

The present method is advantageous as it mitigates the risk of intravitreal injection as the present nanoliposome may be administered by a less risky procedure of subconjunctival injection. Advantageously, subconjunctival injection is able to sustain the release of the hydrophobic drugs from the present nanoliposome which then circumvents the need for frequent topical administration of tacrolimus eye drop(s) and thus avoiding the side effects of frequent topical administration of eye drop(s). Embodiments as described above regarding the nanoliposome and its uses are applicable for the present method of treating anterior segment ocular diseases.

In various embodiments, the nanoliposome administered may have a drug loading of up to 1 mg/ml, 0.5 mg/ml, 0.1 mg/ml, or any other loadings within these ranges. The hydrophobic drug may be a concoction of one or more hydrophobic drugs. The hydrophobic drug may comprise or consist of tacrolimus.

The hydrophobic drug may be encapsulated in the nanoliposome, wherein the nanoliposome has at least one lipid bilayer of the nanoliposome where the hydrophobic drug (e.g. tacrolimus) is encapsulated as described above.

The plurality of unsaturated and/or saturated lipids of the nanoliposome administered may be selected from the group consisting of phosphocholines and sphingolipids. The phosphocholines may be selected from the group consisting of egg yolk phosphatidylcholine (EggPC), 1-palmitoyl-2-oleoyl-sn-glycero-3-phosphocholine (POPC), 1,2-dioleoyl-sn-glycero-3-phosphocholine (DOPC) and dipalmitoylphosphatidylcholine (DPPC). The constituents of EggPC have been described above. Other suitable phosphocholines may be used to form the at least one lipid bilayer of the nanoliposome. Meanwhile, sphingolipids may include sphingomyelins, sphingosines, ceramides etc.

In preferred embodiments, the plurality of unsaturated and/or saturated lipids may comprise or consist of at least one unsaturated lipid constituting more than 50 wt % of the at least one lipid bilayer.

As disclosed above, nanoliposomes of preferred embodiments demonstrate better sustained release of hydrophobic drug(s) (e.g. tacrolimus) over prolonged periods (e.g. several days) when they possess an unsaturated lipid tail attached to a PC "head" as the major constituent. In other words, the at least one unsaturated lipid constituting more than 50 wt % of the at least one lipid bilayer may be composed of a phosphatidylcholine (PC) that incorporates choline as a head group.

Depending on the type of unsaturated or saturated lipids utilized, the nanoliposome administered may have different sizes before or after storage. The size of the nanoliposome may change insignificantly after storage.

The nanoliposome administered may have an average size of 80 nm to 150 nm, 85 nm to 110 nm before storage (e.g. storing at 4° C.). Embodiments concerning other sizes or range of sizes before storage have been described above. Non-limiting embodiments based on EggPC and DPPC liposomes are also described above.

The nanoliposome administered may have an average size of 90 nm to 120 nm after storage (e.g. at 4° C.). Embodiments concerning other sizes or range of sizes after storage (e.g. at 4° C.) have been described above. Non-limiting embodiments based on EggPC and DPPC liposomes are also described above.

As explained above, the type of lipids used may influence the polydispersity index of the nanoliposome to be administered. The polydispersity of the nanoliposome may change insignificantly after storage. In various embodiments, the nanoliposome administered may have a polydispersity index of less than 0.3, 0.2 or even 0.1 before and after storage. Non-limiting embodiments based on EggPC nanoliposomes and DPPC nanoliposomes before and after storage have been described above.

The nanoliposome administered may be a multilamellar vesicle or an unilamellar vesicle according to various embodiments as described above.

In all the embodiments described herein, the anterior segment ocular diseases may refer to ocular inflammatory diseases, ocular surface diseases, and diseases or disorders associated with lack of immunosuppression (e.g. ocular graft rejection).

In summary, the present disclosure relates to nanoliposomes for use in the delivery of tacrolimus to treat various inflammatory diseases or disorders of the eye, ocular surface diseases and in immunosuppression for preventing ocular graft rejection (e.g. post corneal graft).

The nanoliposomes may be prepared from lipids such as, but are not limited to, phosphocholines and sphingolipids. More specifically, the nanoliposomes containing tacrolimus in desired loading concentrations may be prepared by passive loading techniques.

Advantageously, the drug loaded nanoliposomes may be applied via subconjunctival injections and may sustain the release of drugs over an extended duration (days to months). This drastically improves patient compliance as well as minimizes side effects associated with frequent topical instillations (e.g. eye drops) to halt the progression of diseases.

The nanoliposomes may be referred to as a composition of liposomal matter that comprises or consists of saturated and/or unsaturated lipids. The encapsulated drug loading in each of the liposomes may be up to 1 mg/ml and the drug/lipid weight ratio may be up to 0.2. This composition advantageously sustains the release of tacrolimus beyond two weeks.

While the methods described above are illustrated and described as a series of steps or events, it will be appreciated that any ordering of such steps or events are not to be interpreted in a limiting sense. For example, some steps may occur in different orders and/or concurrently with other steps or events apart from those illustrated and/or described herein. In addition, not all illustrated steps may be required to implement one or more aspects or embodiments described herein. Also, one or more of the steps depicted herein may be carried out in one or more separate acts and/or phases.

EXAMPLES

The present invention relates to nanoliposomes for sustained delivery and/or release of tacrolimus for treatment of ocular diseases. Based on the examples described below, high loading concentrations of tacrolimus in nanoliposomes were achieved using a passive loading technique. In addition, controlled and sustained release of tacrolimus from the nanoliposomes were achieved in an in vitro dialysis. The examples demonstrated the release of drug was sustained beyond two weeks based on the in vitro dialysis.

Figure 5:
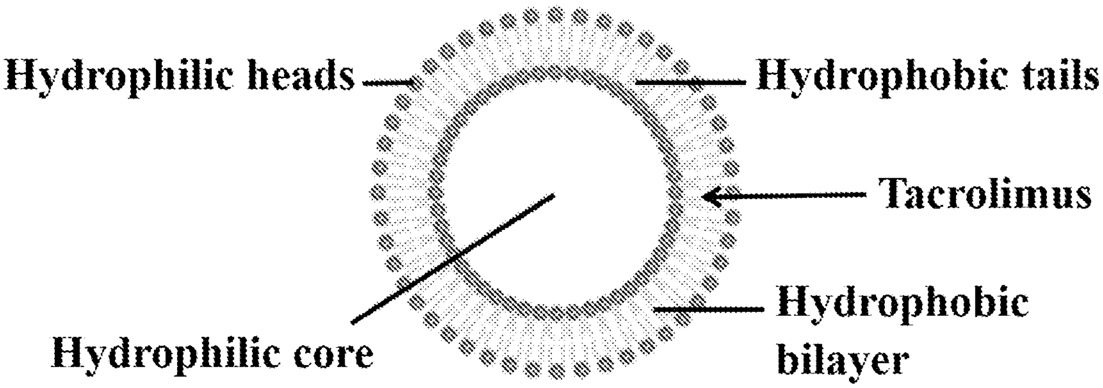
FIG. 5 shows a non-limiting exemplary embodiment of the nanoliposome as disclosed herein. Specifically.

Further, the examples below exemplify encapsulation of tacrolimus in high loading concentrations in the nanoliposomes, where a desirably high drug/lipid (D/L) weight ratio of up to 0.2 is achieved for both unstaturated and saturated liposomes. When the D/L ratio exceeds 0.2, the encapsulation efficiency for the drug decreases, thereby resulting in the lost of drugs from the nanoliposomes. An example of how tacrolimus is encapsulated in the nanoliposome is shown in FIG. 5.

Example 1: Preparation of Tacrolimus Loaded Liposomes

Lipids were weighed and placed in a vacuum desiccator for 1 hour to remove any residual moisture before weighing. The drug, tacrolimus, was also desiccated before weighing. Each batch of liposome was prepared in 5 ml, with an initial lipid concentration of 18 millimolar (mM).

The weighed lipids and drug were then mixed in a round bottom flask, and dissolved in an organic phase mixture that contained methanol and chloroform in a ratio of 1:2. The flask was then maintained in a water bath temperature of 40° C. and rotated in a rotary operator under reduced pressure for 1 hour to remove the organic phase, ultimately leaving behind a thin drug loaded lipid film covering the bottom of the flask. To the thin lipid film, 5 ml of phosphate buffer solution (PBS of pH 7.4) was added to instantaneously form drug loaded multilamellar vesicles (MLVs).

The liposomes' (MLVs) sizes were reduced by extrusion through polycarbonate filter membranes in the corresponding size sequence of 0.2 μm (5 times), and 0.08 μm (10 times) using a bench top extruder purchased from Northern Lipids Inc, Canada. After these extrusion steps, the drug loaded large unilamellar vesicles (LUVs) with a size distribution of about 100±20 nm were formed.

Example 2: Partition Coefficient Measurements

Hydrophobic drugs, such as tacrolimus, distribute between the lipid bilayer and continuous phase of the buffer based on the drugs' solubility. Partition coefficient was calculated based on the ratio of concentrations measured between these two phases. Partition coefficient values were estimated from MLVs prior to the extrusion step.

Briefly, MLVs in microfuge tubes were centrifuged at 13000 rotation per minute (rpm) or 16249 relative centrifugal force (rcf) for half an hour. A clear separation of the lipid pellet from the supernatant was possible due to the micron sized vesicles. The supernatant was visually clear and this showed a complete separation was possible.

The total amount of drug(s) in the MLVs and the amount of drug(s) in the supernatant were estimated by high performance liquid chromatography (HPLC). A continuous (buffer) phase drug(s) amount was calculated from the drug measured in the supernatant. The amount of drug partitioned into the bilayer is calculated by subtracting the drug measured in the supernatant from the total drug amount. The drug partition coefficient (P.C.) in MLVs was then estimated using the following expression given below.

$$P.C. = \frac{\text{Total amount of drug} - \text{amount of drug in buffer}}{\text{Amount of drug in buffer}}$$

Example 3: Measurement of Entrapped Drug Concentration

Generally, the various liposome samples were broken with isopropyl alcohol (IPA) in a volume ratio of 1:5 (liposome:IPA) and then diluted with PBS of pH 7.4. The HPLC method was used to measure the drug concentration of liposomes while taking into consideration the dilution factor and comparing against the standard of tacrolimus in PBS of pH 7.4.

Example 4: In Vitro Drug Release Study And Actual Drug Release Per Day

A dialysis method was used to evaluate release of tacrolimus from liposomal nanocarriers. In the examples, the receptor medium was physically separated from the drug loaded liposomes by a dialysis membrane. The released drug concentration was evaluated from the receptor medium over time by HPLC. For this example, 1 ml of the drug loaded liposomes were filled into a cellulose ester dialysis bag (with a molecular weight cut-off (MWCO) of 100 kD) and clipped by dialysis clips on both ends. 40 ml of PBS buffer at a pH of 7.4 (137 mM NaCl, 2.68 mM KCl, 1.76 mM $KH_2PO_4$, 10.14 mM $Na_2HPO_4$) was measured and taken in an amber bottle. The dialysis bags was suspended in the PBS buffer and placed in an incubator at a temperature of 37° C. 2 ml of dialysis medium was sampled out every day and the entire PBS medium was replenished daily. The amount of drug(s) released over time was measured using HPLC and presented as a cumulative percentage release plotted against time.

Example 5: Characterization of Drug Loaded Liposomes—Size Stability Studies

The average size as well as the size distribution (polydispersity index) of the liposomes were characterized by using Malvern Zetasizer Nano ZS. The particle sizes were measured after preparation and continuously monitored during storage (4° C.).

Example 6a: Results—In Vitro Size Stability of Tacrolimus in Unsaturated Liposomes (EggPC Liposomes)

The unsaturated liposomes were based on egg yolk phosphatidylcholine (EggPC) liposomes. EggPC contains, without being limited to, POPC, phosphatidylethanolamine, DPPC, DOPC and sphingomyelins etc. The EggPC liposomes have a D/L weight ratio of 0.2 with a drug (tacrolimus) loading concentration of 1 mg/ml. The loading concentration may depend on what is required to adequately deliver daily amounts over several days.

The changes in the size of the liposomes upon and during storage were continuously monitored with Zetasizer (Malvern Instruments, Malvern, UK). As shown in Table 1 below, tacrolimus loaded EggPC liposomes were found to be stable for at least one month in storage at 4° C. and the average size ($Z_{avg}$) of the liposomes were found to be about 90 nm with a narrow polydispersity index (PDI) of less than 0.1.

TABLE 1

Size Measurements of Tacrolimus Loaded EggPC Liposomes Immediately After Extrusion And One Month After Storage At 4° C.
EggPC/Tacrolimus LUV
D/L weight ratio of 0.2
Initial Drug Concentration of 1 mg/ml

| Days | $Z_{avg}$ - Zeta size (average) (nm) | PDI |
|---|---|---|
| 0 | 89.64 ± 0.78 | 0.052 ± 0.018 |
| 30 | 90.67 ± 0.49 | 0.014 ± 0.007 |

Example 6b: Results—In Vitro Drug Release Study of Tacrolimus in Unsaturated Liposomes (EggPC Liposomes)

The release of tacrolimus from EggPC liposomes was evaluated by a dialysis technique and expressed in terms of cumulative drug release (%) over time as shown in FIG. 1. In FIG. 1, the in vitro drug release studies (1 ml of liposomes dialysed against 40 ml of PBS with pH of 7.4) for three independent samples of tacrolimus loaded EggPC liposomes as carried out are shown. All three samples were of the same drug loading and D/L ratio.

The release of tacrolimus from the liposomes was sustained beyond two weeks in vitro (approximately 60%), albeit a burst release was observed in the first few days.

Example 6c: Results—In Vitro Drug Release Study of Tacrolimus in Unsaturated Liposomes (POPC Liposomes)

Figure 2:
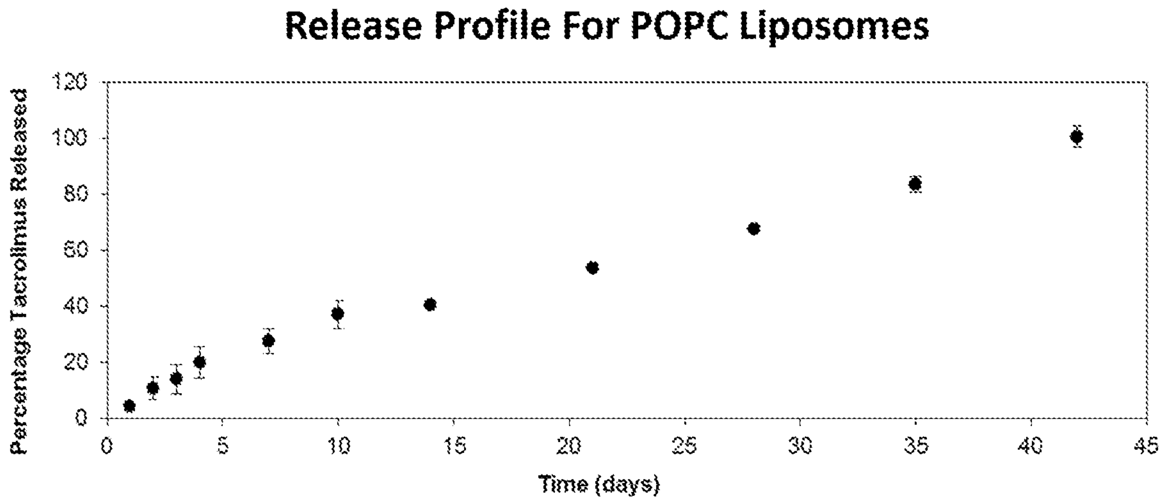
FIG. 2 shows a cumulative percentage tacrolimus release (%) plot against time (days). This plot features an in vitro drug release profile of tacrolimus loaded 1-palmitoyl-2-oleoyl-sn-glycero-3-phosphocholine (POPC) liposomes for three independent samples made according to the embodiments disclosed herein. For each sample, 1 ml of liposomes was dialysed against 40 ml PBS with a pH of 7.4. Each data point represents an average reading of the three samples.

The unsaturated liposomes in this example were based on 1-palmitoyl-2-oleoyl-sn-glycero-3-phosphocholine (POPC). The release of tacrolimus from these liposomes was evaluated by the dialysis technique as described above and expressed in terms of cumulative drug release (%) over time as shown in FIG. 2. In FIG. 2, the in vitro drug release studies for three independent samples of tacrolimus loaded POPC liposomes (1 ml of liposomes dialysed against 40 ml of PBS with pH of 7.4) as carried out are shown. The cumulative percentage of tacrolimus release was then plotted against time (days). The almost-complete release of tacrolimus from POPC was sustained for 42 days in vitro with a suppressed burst observed in the first few days. The drug loading concentrations and D/L ratios for POPC liposomes are the same as EggPC.

Figure 3:
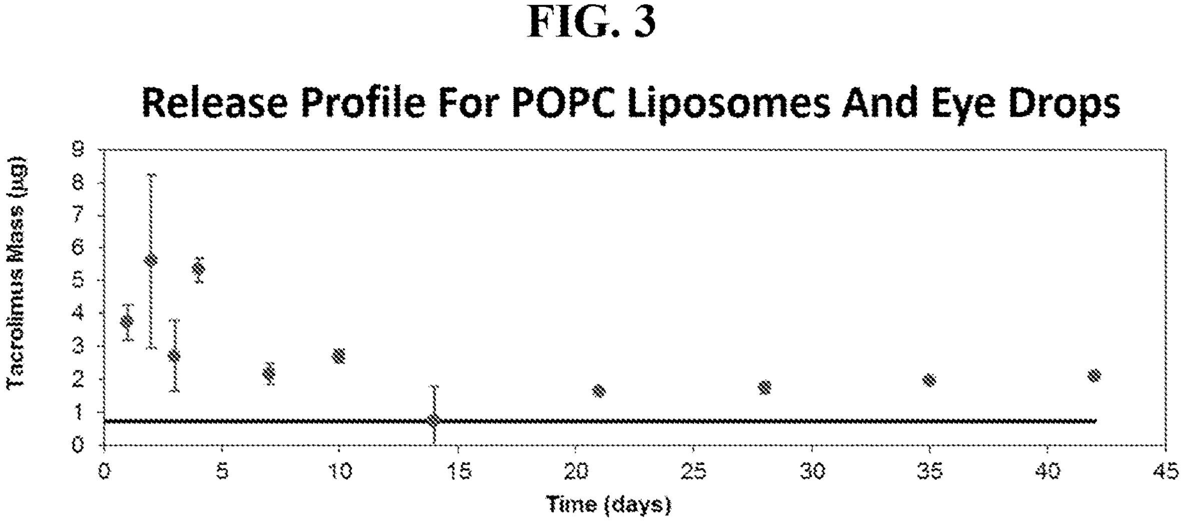
FIG. 3 shows the in vitro drug release profile of tacrolimus loaded POPC liposomes for three independent samples. The daily (calculated) tacrolimus mass release (μg) was plotted against time (days). For each sample, 1 ml of liposomes was dialysed against 40 ml PBS with a pH of 7.4. The release profile of tacrolimus based on eye drops is also included in FIG. 3 as represented by the solid flat line. Each data point represents an average reading of the three samples.

A comparison of tacrolimus release profiles between tacrolimus eye drop(s) and tacrolimus POPC liposome is shown in FIG. 3. In FIG. 3, the in vitro drug release studies for three independent samples of tacrolimus loaded POPC liposomes (1 ml of liposomes dialysed against 40 ml of PBS with pH 7.4) as carried out are shown. Daily (calculated) tacrolimus mass release profile was plotted against time (days) as shown in FIG. 3. The release profile of tacrolimus based on eye drops is also included in FIG. 3 as represented by the solid flat line.

Compared to conventional regimen(s) for tacrolimus eye drops where a daily release rate of 0.72 μg/day is needed (represented as a solid flat line in FIG. 3), it is observable that in vitro tacrolimus release from liposomes of the present disclosure meets or even exceeds the conventional release target for the entire duration of sustained release. Based on these results, the present liposomes not only circumvent the issues associated with tacrolimus eye drops but also provide an improved duration of sustained drug delivery.

Example 7a: Results—In Vitro Size Stability of Tacrolimus in Saturated Liposomes (DPPC Liposomes)

The saturated liposomes were based on dipalmitoylphosphatidylcholine (DPPC) liposomes prepared according to example 1. The DPPC liposomes have a D/L weight ratio of 0.2 with a drug (tacrolimus) loading concentration of 1 mg/ml. As shown in Table 2 below, drug loaded DPPC liposomes were stable in size for at least 1 month storage at 4° C.

TABLE 2

Size Measurements of Tacrolimus Loaded DPPC Liposomes Immediately After Extrusion And One Month After Storage At 4° C.
DPPC/Tacrolimus LUV
D/L weight ratio of 0.2
Initial Drug Concentration of 1 mg/ml

| Days | $Z_{avg}$ - Zeta size (average) (nm) | PDI |
|---|---|---|
| 0 | 106.37 ± 1.00 | 0.28 ± 0.016 |
| 30 | 112.8 ± 1.05 | 0.218 ± 0.036 |

From Table 2, the average size ($Z_{avg}$) of the liposomes were found to be about 110 nm with a narrow polydispersity index (PDI) of less than 0.3.

Example 7b: Results—In Vitro Drug Release Study of Tacrolimus in Saturated Liposomes (DPPC Liposomes)

Figure 4:
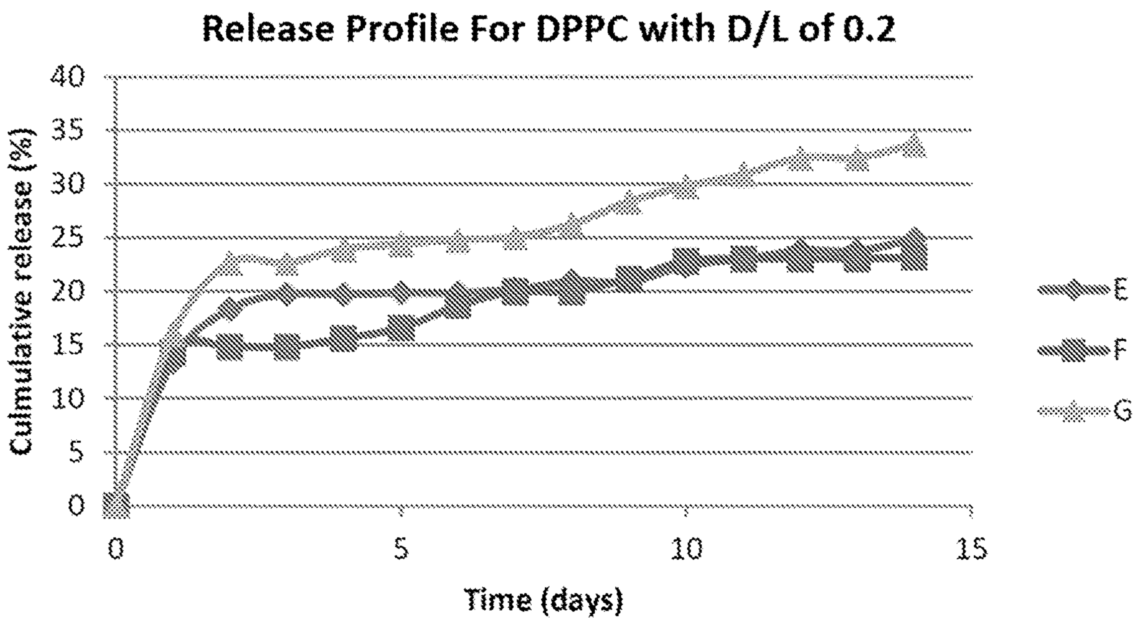
FIG. 4 shows a cumulative tacrolimus release (%) plot against time (days). This plot features an in vitro drug release profile of tacrolimus loaded dipalmitoylphosphatidylcholine (DPPC) liposomes for three independent samples (labelled as E, F and G) made according to the embodiments disclosed herein. For each sample, 1 ml of liposomes was dialysed against 40 ml PBS with a pH of 7.4.

The release of tacrolimus from DPPC liposomes was evaluated by the dialysis technique as described above and expressed in terms of cumulative drug release (%) over time as shown in FIG. 4. In FIG. 4, the in vitro drug release studies (1 ml of liposomes dialysed against 40 ml of PBS with pH of 7.4) for three independent samples of tacrolimus loaded DPPC liposomes as carried out are shown. The cumulative tacrolimus release (%) was plotted against time (days). For each. The release of tacrolimus from liposomes was sustained beyond two weeks in vitro (about 35%), albeit a smaller burst observed in the first few days. In comparison with EggPC liposomes, DPPC liposomes has a smaller initial burst and only about 35% of the drug is released at the end of two weeks compared to EggPC liposomes (about 60%).

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A method of preventing and/or treating anterior segment ocular diseases by administering a nanoliposome comprising a plurality of unsaturated and/or saturated lipids forming at least one lipid bilayer encapsulating a hydrophobic drug comprising tacrolimus, wherein the hydrophobic drug and the plurality of saturated and/or unsaturated lipids have a weight ratio of up to 0.2, and wherein the plurality of unsaturated and/or saturated lipids comprise at least one unsaturated lipid constituting more than 50 wt % of the at least one lipid bilayer.

2. The method according to claim 1, wherein the nanoliposome is administered by subconjunctival injection.

3. The method according to claim 1, wherein the nanoliposome administered has a drug loading of up to 1 mg/ml.

4. The method according to claim 1, wherein the plurality of unsaturated and/or saturated lipids of the nanoliposome administered are selected from the group consisting of phosphatidylcholines and sphingolipids.

5. The method according to claim 4, wherein the phosphatidylcholines are selected from the group consisting of egg yolk phosphatidylcholine (EggPC), 1-palmitoyl-2-oleoyl -sn-glycero-3-phosphocholine (POPC), 1,2-dioleoyl-sn-glycero-3-phosphocholine (DOPC) and dipalmitoylphosphatidylcholine (DPPC).

6. The method according to claim 1, wherein the nanoliposome administered has an average size of 80 nm to 150 nm before storing at 4° C.

7. The method according to claim 1, wherein the nanoliposome administered has an average size of 9nm to 120 nm after storing at 4° C.

8. The method according to claim 1, wherein the nanoliposome administered has a polydispersity index of less than 0.3 before and after storing at 4° C.

9. The method according to claim 1, wherein the nanoliposome administered is a multilamellar vesicle or an unilamellar vesicle.

10. The method according to claim 1, wherein (i) the hydrophobic drug and (ii) the plurality of saturated and unsaturated lipids have a weight ratio of up to 0.2, wherein the plurality of unsaturated and saturated lipids consist at least one unsaturated lipid as a major component of the at least one lipid bilayer and the saturated lipids as a minor component of the at least one lipid bilayer, wherein the at least one unsaturated lipid as the major component constitutes more than 50 wt % of the at least one lipid bilayer, wherein the at least one unsaturated lipid consists of egg yolk phosphatidylcholine (EggPC) and 1-palmitoyl-2-oleoyl-sn-glycero-3-phosphocholine (POPC), wherein the nanoliposome formed of egg yolk phosphatidylcholine (EggPC) and 1-palmitoyl-2-oleoyl-sn-glycero-3-phosphocholine (POPC) sustains release of the hydrophobic drug for at least 2 weeks with at most 60 % of the hydrophobic drug released in 2 weeks and with initial burst release of the hydrophobic drug suppressed, as measured by an in vitro release assay at a pH of 7.4 and in a phosphate buffer solution.

11. The method according to claim 1, wherein the plurality of unsaturated and/or saturated lipids consist of 1-palmitoyl-2-oleoyl-sn-glycero-3-phosphocholine (POPC).

* * * * *